United States Patent
Andersson

(10) Patent No.: US 7,767,141 B2
(45) Date of Patent: Aug. 3, 2010

(54) METHOD FOR REDUCING ALLERGENS IN AN ENCLOSURE

(75) Inventor: Goran B. Andersson, Williamsville, NY (US)

(73) Assignee: Pure Solutions LLC, Williamsville, NY (US)

( * ) Notice: Subject to any disclaimer, the term of this patent is extended or adjusted under 35 U.S.C. 154(b) by 0 days.

(21) Appl. No.: 12/607,159

(22) Filed: Oct. 28, 2009

(65) Prior Publication Data

US 2010/0047118 A1 Feb. 25, 2010

Related U.S. Application Data

(63) Continuation of application No. 11/248,355, filed on Oct. 12, 2005, now abandoned.

(60) Provisional application No. 60/617,704, filed on Oct. 12, 2004.

(51) Int. Cl.
*A61L 9/00* (2006.01)
*A61L 2/20* (2006.01)
*A61L 2/00* (2006.01)

(52) U.S. Cl. .................. 422/4; 422/1; 422/33; 422/120

(58) Field of Classification Search ...................... 422/1, 422/4, 33, 120; 95/273
See application file for complete search history.

(56) References Cited

U.S. PATENT DOCUMENTS

2001/0004813 A1 6/2001 Hedman

2004/0028554 A1 * 2/2004 Hedman ...................... 422/24

FOREIGN PATENT DOCUMENTS

EP 1424932 B1 6/2007
WO 9822152 A1 5/1998

* cited by examiner

*Primary Examiner*—Sean E Conley
*Assistant Examiner*—Kevin C Joyner
(74) *Attorney, Agent, or Firm*—Hodgson Russ LLP

(57) ABSTRACT

Provided is a method for reducing the amounts of fungal spores and small airborne particles in an enclosure, where the enclosure has or is in communication with an air handling system. The method comprises the steps of applying vacuum suction to the air handling system and contacting the air handling system with a first antimicrobial agent; applying a cleansing agent to the carpets and upholstery in the enclosure; fogging the enclosure with a second antimicrobial agent; releasing ozone within the enclosure for a period of time and terminating the release of ozone to allow the ozone concentration to return to normal levels; placing a reservoir containing tea tree oil into the air handling system, and initiating operation of an air purifier air in the enclosure, wherein for a period of at least 90 days, the airborne particles in the enclosure are fewer than 1.0 million airborne particles per cubic meter of air; the airborne fungal spores in the enclosure an amount at least 1.1 times below the amount of airborne fungal spores in the air outside the enclosure before performing the method; and, the surface fungal spores in the enclosure are at least 3.0 times below the surface level of fungal spores in the enclosure before performing the method.

19 Claims, No Drawings

METHOD FOR REDUCING ALLERGENS IN AN ENCLOSURE

This application is a continuation of application Ser. No. 11/248,355, filed Oct. 12, 2005,now abandoned which in turn claims priority to U.S. provisional application No. 60/617,704, filed on Oct. 12, 2004, the disclosures of each of which are incorporated herein by reference.

FIELD OF THE INVENTION

The present invention relates generally to the field of reducing allergens from an enclosure.

BACKGROUND OF THE INVENTION

The EPA estimates that indoor air may be as much as 70-100 times more polluted than outside air and has ranked indoor air pollution among its top five public health risks. Indoor air is a source of allergens and indoor air pollution is of particular concern to asthma and allergy sufferers, children and the elderly. At high levels, indoor air pollution poses a health risk to the general population. Another source of allergens are air handling units since often they do not filter the air they circulate through the building and/or take in from the outside. While conventional steps may be taken to remove allergens from regularly occupied rooms and buildings, such steps must be frequently repeated to maintain reduced allergen levels. Therefore, there is a need for a method of reducing the amount of allergens in a room or building that will result in reduced amounts of allergens over a prolonged period of time.

SUMMARY OF THE INVENTION

The present invention provides a method for reducing allergens, such as fungal spores and small airborne particles (i.e., particles having diameters of between 0.3 and 2.5 microns), in an enclosure for a period of at least ninety days.

The method is performed by vacuuming and contacting an air handling system in or in communication with the enclosure with a first antimicrobial agent.

Subsequently, the carpets and upholstery are subjected to vacuum through a High-Efficiency Particulate Air (HEPA) filter.

A formulation comprising a cleansing agent is then applied to the carpets and upholstery in the enclosure, wherein the cleansing agent contains a composition comprising a non-ionic surfactant, benzlkonium chloride, 2-propanol, or Di-n-alkyl ($C_8$-$C_{10}$)-N,N-dimethylammonium chloride.

After the cleansing agent is applied, the enclosure is fogged with a formulation containing a composition comprising a second antimicrobial agent, where the second microbial agent is an aqueous organosilane, a quaternary chloride or a hydantoin resin.

Ozone is then released within the enclosure for a period of time, after which the ozone release is terminated and the ozone concentration is allowed to return to normal levels.

After the ozone level has returned to a normal level, a reservoir containing tea tree oil is placed into the air handling system and the air handling system is placed into operation. Additionally, air in the enclosure is circulated through an air purifier which contains a HEPA filter and an activated carbon filter.

The method is such that, for a period of at least 90 days, the airborne particles in the enclosure are maintained at fewer than 1.0 million airborne particles per cubic meter of air; the amount of airborne fungal spores in the enclosure is at least 1.1 times below the amount of airborne fungal spores in air outside the enclosure; and, the amount of surface fungal spores in the enclosure is at least 3.0 times below the amount of surface fungal spores in the enclosure before performing the method of the invention.

DETAILED DESCRIPTION OF THE INVENTION

In the present invention is provided a method for reducing the amount of allergens in an enclosure such that the reduced amount of allergens is maintained over a period of at least ninety days. In particular, the method achieves a reduction in the amount of allergens which are airborne fungal spores, surface fungal spores and airborne particles.

"Fungal spores" as used herein include the spores of any member of the kingdom Fungi, including the yeasts, molds, mildew and mushrooms. "Airborne particles" as used herein are airborne particles of a size of between 0.3-2.5 microns in diameter. It is also expected that the amount of bacteria and viruses in the enclosure will be reduced.

The method of the invention is suitable for use in an enclosure which is in communication with an air handling system. The air handling system is considered to be in communication with the enclosure when air inside the enclosure or air in fluid communication with air inside the enclosure can be caused to flow by the air handling system. An "air handling system" as used herein means a system that can cause air to flow in an enclosure and which system is capable of regulating the temperature of the air in the enclosure. Accordingly, air handling systems include self-contained air conditioner units located partially or completely within an enclosure. Examples of such air handling systems are those typically mounted in a window of a home or hotel room, which are also generally referred to in the art as personal temperature air conditioners, or "PTACs." Also included within the meaning of "air handling system" is ductwork and an air temperature control device connected to the ductwork, which device may be external to the enclosure, and which can cause air to flow through the ductwork into the enclosure and regulate the temperature of the air flowing into the enclosure. Examples of such air temperature control devices include conventional furnaces and central air conditioning units.

The method of the invention comprises the steps of:

a) applying vacuum suction to the air handling unit;

b) applying an aqueous solution comprising a first antimicrobial agent to the air handling system using forced air;

c) applying vacuum suction to the carpets and upholstery in the enclosure with a vacuum cleaner fitted with a High-Efficiency Particulate Air (HEPA) filter;

d) applying a formulation comprising a cleansing agent to the carpets and upholstery in the enclosure, where the cleansing agent is a composition comprising a non-ionic surfactant, benzlkonium chloride, 2-propanol, or Di-n-alkyl ($C_8$-$C_{10}$)-N,N-dimethylammonium chloride;

e) fogging surfaces in the enclosure with a formulation comprising a second antimicrobial agent, where the second antimicrobial agent is a composition comprising an aqueous organosilane, a quaternary chloride or a hydantoin resin;

f) releasing ozone within the enclosure at a rate of at least 4 parts per million (ppm) for at least one hour;

g) terminating the release of ozone and allowing the ozone concentration in the enclosure to reduce to below 0.05 ppm;

h) placing a reservoir containing tea tree oil into the air handling system;

i) initiating operation of the air handling system; and j) initiating operation of an air purifier, which air purifier comprises a HEPA filter and an activated carbon filter, and wherein the air in the enclosure circulates through the air purifier for at least three changes per hour. It is preferable that the air purifier be operated continuously thereafter. It is also preferable that steps a) through j) be carried out within a twenty-four hour period.

The method is such that, ninety days after initiating operation of the air purifier, the airborne particles in the enclosure are fewer than 1.0 million per cubic meter of air, preferably fewer than 500,000, and more preferably fewer than 300,000 per cubic meter of air; the airborne fungal spores in the enclosure are an amount at least 1.1 times below, and preferably at least 1.5 times below, the amount of airborne fungal spores outside the enclosure before performing steps a) through j); and, the surface fungal spores in the enclosure are at least 3 times below, and preferably at least 5 times below, the amount of surface fungal spores in the enclosure before performing steps a) through j).

We have empirically determined it is important to perform steps a) and b) prior to the subsequent steps. This sequence is critical because the application of the first antimicrobial agent by forced air displaces a significant amount of contaminants from the air handling unit into the enclosure, even after application of vacuum of step a).

In respect of applying the first antimicrobial agent to the air handling system, any antimicrobial agent can be used. However, it is preferable to use an antimicrobial agent with a broad spectrum of activity such that bacteria, viruses and fungi can be killed when contacted by the first antimicrobial agent. For example, suitable first antimicrobial agents include compositions comprising 2-bromo-2-nitropropane-1,3-diol. Such compositions are commercially available and are typically applied as a solution having a 2-bromo-2-nitropropane-1,3-diol concentration of about 0.02% by weight.

The first antimicrobial agent is applied by spraying a mixture of the agent and water into the air handling unit using forced air. Suitable forced air blowers are commercially available. It is generally preferred to use at least 110 pounds per square inch of pressure when applying the first antimicrobial agent. Further, it is preferable to contact as much of the air handling system surfaces as possible with the first antimicrobial agent, particularly air intake and outlet ports, fan blades and heat exchange tubing.

In air handling system configurations where the temperature regulating device is in communication with the enclosure via ductwork, both the ductwork and the temperature regulating device are contacted with the first antimicrobial agent. It is preferable to contact as much of the ductwork and temperature control device surfaces as possible.

Subsequent to application of the first antimicrobial agent to the air handling system, the carpets and upholstery are subjected to vacuum to remove dust and debris. The vacuuming can be performed with any commercially available vacuum cleaner that is fitted with a HEPA filter. It is preferable to vacuum substantially all of the carpeting and upholstery in the enclosure. Further, in one embodiment, non-fabric surfaces in the room are also vacuumed, including any non-upholstered furniture, ceilings, walls, tiling, mirrors, porcelain, etc.

After vacuuming, the carpets and upholstery in the room are contacted with a formulation comprising a cleansing agent. The cleansing agent may be a composition comprising non-ionic surfactants, benzlkonium chloride, 2-propanol, or Di-n-alkyl ($C_8$-$C_{10}$)-N,N-dimethylammonium chloride.

In one embodiment, the non-ionic surfactant is used. Preferred non-ionic surfactants are polyoxyethylene fatty acid esters, particularly those having the formula RCOO(CHCH) nH, wherein R is a long chained alkyl group. One example of a preferred non-ionic surfactant is a formulation comprising didecyl dimethyl ammonium chloride. A more preferred formulation comprises didecyl dimethyl ammonium chloride and a hydrogen peroxide solution. An example of such a formulation is disclosed in U.S. Pat. No. 6,530,384.

It is preferable to contact substantially all of the carpeting and upholstery in the enclosure with the formulation comprising the cleansing agent. The formulation comprising the cleansing agent can be applied to the carpets and the upholstery using a conventional carpet cleaning machine or upholstery cleaning machine, respectively. Further, the formulation comprising the cleansing agent may also be applied to bedding, and/or wiped onto to non-porous surfaces, such as walls, ceilings, non-upholstered furniture, mirrors, etc.

Subsequent to application of the formulation comprising the cleansing agent, a formulation comprising a second antimicrobial agent is applied to the exposed surfaces in the enclosure. It is preferable to apply the formulation comprising the second antimicrobial agent by fogging the enclosure with the formulation and therefore fogging exposed surfaces in the enclosure. By fogging it is meant that the formulation is applied as a suspension of droplets in a gas. Fogging the enclosure can be performed using a commercially available ultra-low-volume (ULV) cold fogger or by any conventional fogging technique.

It is preferable to contact as much surface area of the enclosure and as much surface area of items in the enclosure as possible with the formulation comprising the second antimicrobial agent. Accordingly, in one embodiment, carpeting, curtains, walls, ceilings, furniture, bedding, mirrors, appliances, etc., are fogged with the formulation comprising the second antimicrobial agent such that substantially all of the exposed surfaces in the enclosure are contacted with the second antimicrobial agent.

The second antimicrobial agent may be an aqueous organosilane, a quaternary chloride or a hydantoin resin.

When the second antimicrobial agent is an aqueous organosilane, the aqueous organosilane may be any aqueous organosilane. A preferred aqueous organosilane is ocatadecylaminoimethyloomethoxysilylpropyl ammonium chloride. It is preferable to apply this agent as a solution comprising the aqueous organosilane in an amount less than 1.0% by weight, and preferably at 0.75% by weight.

Subsequent to application of the formulation comprising the second antimicrobial agent, ozone is released into the enclosure. It is preferable to release the ozone until the concentration of ozone in the enclosure reaches about 4 ppm. It is more preferred to achieve a concentration of about 8 ppm. This ozone concentration can be achieved by, for example, releasing about 2.7 grams of ozone per hour into an enclosure of up to 40,000 cubic feet for at least two hours.

As will be clear to those skilled in the art, the ozone can be released in any conventional manner, such as by a standard ozone generator. Once the desired ozone concentration has been reached for the desired amount of time, the ozone generator is turned off. After turning off the ozone generator, the ozone decomposes and the ozone concentration reduces to a level below 0.05 ppm. It is preferable to permit the passage of at least 1 to 2 hours to facilitate such ozone decomposition.

After treating the enclosure with ozone, a reservoir containing tea tree oil is placed into the air handling system. The tea tree oil is provided as a composition that can dissipate into the air such that air that is drawn into the air handling system comes into contact with the dissipating tea tree oil. The air handling system accordingly disperses the tea tree oil into the enclosure. It is preferable that the tea tree oil is positioned such that air entering the air handling unit contacts the dissipating tea tree oil prior to flowing over the fan blades and heat exchange tubing typically found in an air handling system. It is believed such positioning maximizes contact between the tea tree oil and surfaces in the air handling system.

The tea tree oil is provided in a reservoir such that the tea tree oil can dissipate through an opening in the reservoir. Without intending to be bound by any particular theory, it is considered that dissipating tea tree oil contacts surfaces of the air handling system and surfaces of the enclosure, thereby inhibiting microbial growth on these surfaces and enhancing the effect of the method.

Tea tree oil is available through a variety of commercial sources. Preferred tea tree oil formulations are provided as gels. More preferred is a pharmaceutical grade tea tree oil formulation provided as an emulsified gel comprising about 8% pure tea tree oil and about 1% lemon tea tree oil. Subsequent to placing the tea tree oil into the air handling system, operation of the air handling system is initiated.

After activating the air handling system, operation of an air purifier in the enclosure is initiated such that air in the enclosure is circulated through the air purifier. The air purifier is one that comprises a HEPA filter and an active carbon filter. It is preferable that the air be circulated through the filter continuously at a flow rate sufficient to enable three changes of air in the enclosure per hour.

The following Example is intended to illustrate the method of the invention and is not meant to be limiting.

Example 1

The method of the invention was performed in a conventional hotel room which was regularly occupied by hotel guests in the normal course of business. The room was approximately 250 square feet in size. Performing the method of the invention on the hotel room is referred to in this Example as "conversion."

Various parameters were analyzed across four test periods. The test periods were:

1) Pre Conversion (prior to performing the method of the invention);

2) Immediate Post Conversion (24 hours after performing the method);

3) 30 Days Post Conversion;

4) 90 Days Post Conversion Conditions

The Immediate Post Conversion period is considered to have begun after the air purifier has been placed into operation.

Test Parameters

Test parameters were divided into two categories: Snap Shot Samples and Continuous Monitoring Samples. Snap Shot Samples are samples taken at a single point in time. Continuous Monitoring Samples are recorded continuously throughout the test period.

All testing was conducted with instrumentation calibrated to National Institute of Standards and Technology parameters. Samples were collected and analyzed in compliance with protocols from the U.S. Environmental Protection Agency, American Conference of Governmental Industrial Hygienists, and American Industrial Hygiene Association. All microbial samples were analyzed by an American Hygiene Association EMLAP certified laboratory. Samples were collected by a trained technician from Indoor Air Professionals, Inc. using standard collection techniques.

Data for various parameters were compared with industry guidelines and standards as promulgated by the above agencies, as well as the American Society of Heating, Refrigeration, and Air Conditioning Engineers.

Snap Shot Samples Results

In Table 1 is provided data regarding airborne fungal spore amounts as they are affected by the method of the invention.

As can be seen from Table 1, in respect of the Pre Conversion period, the total airborne fungal spore count in the room air was 60. This compares with 40 in the outside air sample, indicating an amount of fungal spores of 1.5 times more in the room as compared to outside levels.

For the Immediate Post Conversion period, the total fungal spore count in the room air was 80. This compares with a count of 160 in the outside air sample indicating an amount of airborne fungal spores two times lower in the room as compared to the amount outside the room.

For the 90 Day Post Conversion period, the total fungal spore count in the room air sample was 4. This compares with a total fungal spore count of 585 in the outside air sample, indicating an amount 146 times lower airborne spores in the room as compared to the amount outside the room.

TABLE 1

| | Pre Period outside | Pre Period Inside | Amount1 inside/ outside | Immed. Post Period Outside | Immed. Post Period Inside | Amount outside/ inside | 90 Day Post Outside | 90 Day Post Intside | Amount outside/ inside |
|---|---|---|---|---|---|---|---|---|---|
| Total Fungal Spores | 40 | 60 | 1.5 | 160 | 80 | 2 | 585 | 4 | 146 |

In Table 2 is provided data related to the number of viable surface fungal spores in the room (as determined by colony forming units) compared to pre-conversion amounts of viable surface fungal spores in the room.

As can be seen from Table 2, amounts of viable surface fungal spores decreased during the Immediate Post Period (3.4 fold). During the 30 Day Post Period, amounts continued to remain lower than the Pre Period (2.68 fold). (This Test was not conducted for Test Period 4).

TABLE 2

| | Pre Period | Immediate Post Period | Amount Pre/ Immediate Post | 30 Day Post | Amount Pre/30 Days Post |
|---|---|---|---|---|---|
| Total Fungal Spores | 5,769 | 1,615 | 3.4 | 2,154 | 2.68 |

In Table 3 is provided data related to total surface fungal spores (viable and non-viable) as determined in a swipe sample. As can be seen from Table 3, surface fungal spore amounts, as measured in spores per cubic centimeters, showed a significant decrease during all of the Post Periods as compared to the Pre Period. In this regard, during the Immediate Post Period, total surface fungal spores were reduced by more than 5 fold. During the 30 Day Post Period, amounts were reduced to more than 40 fold compared to the Pre-Period. In the 90 day Post Period, amounts of total surface fungal spores were more than 5 fold lower than the Pre Period.

TABLE 3

|  | Pre Period | Immediate Post Period | Amount Pre/ Immediate Post | 30 Day Post | Amount Pre/ 30 Days Post | 90 Day Post | Amount Pre/ 90 Days Post |
| --- | --- | --- | --- | --- | --- | --- | --- |
| Total Fungal Spores | 7,130 | 1,278 | 5.58 | 169 | 42.19 | 1,586 | 5.5 |

Continuous Monitoring Sampling Results

Results from continuous monitoring of various parameters throughout the test period are provided.

Temperature

Temperature levels averaged 72 degrees F. throughout the test periods indicating maintenance of an acceptable comfort level for occupants.

Relative Humidity

Relative humidity levels were normal (average of 52%) during pre and Immediate Post period. Levels reached a high of 77% on during the conversion period. Levels remained relatively elevated (around 60%) until the day following the conversion and then returned to the normal range. During the 30 Day Post Period, average humidity levels were 60% due to the air handling unit being shut down and higher levels outdoors. During the 90 Day Post Period humidity levels averaged 52%.

Carbon Dioxide

Carbon dioxide levels were sporadic throughout the test periods. The levels trended lower toward the end of the test periods. Carbon dioxide is not a "pollutant" at these levels, but is an indicator of adequate room ventilation. Relatively high levels can be attributed to higher occupancy (as humans exhale carbon dioxide). Measured carbon dioxide levels confirmed there was adequate ventilation in the room.

Small Particles (<2.5 Microns)

Small particles, as measured per cubic meter of air, decreased significantly during the Immediate Post Conversion Period as compared to the Pre Conversion Period. Small particles were relatively high during the Pre Conversion Period (9 million average) and even higher during the conversion period (peak reaching over 20 million). Levels returned to below threshold limits of 1,000,000 after the completion of the conversion. During the Immediate Post Conversion period, particles averaged around 300,000. During the 30 Day Post Conversion Period, small particles spiked initially, however, dropped and remained at lower levels (approximately 30,000) as compared to the Immediate Post Conversion period. During the 90 Day Post Period, small particles were below threshold limits (1 Million average), and 9 times lower than the Pre period.

Total Volatile Organic Compounds (TVOC)

TVOC's did not fluctuate throughout the duration of the monitoring periods and remained within acceptable limits during all the test periods. During the 30 and 90 Day Post periods, levels increased, but were still below the threshold levels.

Carbon Monoxide

Carbon Monoxide levels remained within acceptable limits throughout the test periods.

Radon

Radon levels remained well below threshold levels throughout the duration of the periods.

Ozone

High levels of ozone were recorded during the application of the ozone treatment during the conversion process. Otherwise levels were well below 0.05 ppm during the pre and post periods. Importantly, the high levels dissipated quickly once the ozone equipment was turned off.

Thus, by practicing the method of the invention in a hotel room with normal occupancy for a period of ninety days, the following was observed:

Amounts of airborne fungal spores were significantly lower during the Post Periods as compared to the Pre Period; amounts of surface fungal organisms were significantly lower during the Post Periods as compared to the Pre Period; small airborne particles were significantly lower during the Post Periods as compared to the Pre Periods; other potential indoor air quality parameters such as radon, ozone, large particles, and total volatile organic compounds were maintained within acceptable ranges; ventilation remained adequate; and, temperature and humidity were maintained within normal comfort ranges.

While this invention has been illustrated via the embodiments described herein, routine modifications will be apparent to those skilled in the art, which modifications are intended to be within the scope of the invention.

I claim:

1. A method for reducing allergens in an enclosure, wherein the allergens are selected from the group consisting of airborne particles, airborne fungal spores and surface fungal spores, and wherein air in the enclosure is in communication with an air handling system, comprising the steps of:
   a) applying vacuum suction to the air handling system;
   b) applying to the air handling system an aqueous solution comprising a first antimicrobial agent wherein the solution is applied using forced air;
   c) applying vacuum suction to carpets and upholstery in the enclosure with a vacuum cleaner fitted with a High-Efficiency Particulate Air (HEPA) filter;
   d) applying a formulation comprising a cleansing agent to the carpets and upholstery in the enclosure, wherein the cleansing agent is a composition comprising a non-ionic surfactant, benzlkonium chloride, 2-propanol, or Di-n-alkyl ($C_8$-$C_{10}$)-N,N-dimethylammonium chloride;
   e) fogging surfaces in the enclosure with a formulation comprising a second antimicrobial agent, wherein the second antimicrobial agent is a composition comprising an aqueous organosilane, a quaternary chloride or a hydantoin resin;
   f) releasing ozone within the enclosure at a rate of at least 2 parts per million (ppm) for at least one hour;
   g) terminating the release of ozone and allowing the ozone concentration in the enclosure to return to below 0.05 ppm;
   h) placing a reservoir containing a composition comprising tea tree oil into the air handling system, such that when the air handling system is operated, the tea tree oil is dispersed into the enclosure;

wherein the tea tree oil can dissipate such that air that is drawn into the air handling system comes into contact with the dissipating tea tree oil and disperses the tea tree oil into the enclosure;

i) initiating operation of the air handling system; and j) initiating operation of an air purifier, which air purifier comprises a (HEPA) filter and an active carbon filter;

wherein, after initiating operation of the air purifier of step j, and for a period of at least 90 days, the airborne particles in the enclosure are fewer than 1.0 million airborne particles per cubic meter of air; and the airborne fungal spores in the enclosure are present in an amount at least 1.1 times below the amount of airborne fungal spores in the air outside the enclosure before performing steps a) through j); and, the amount of surface fungal spores present in the enclosure is at least 3.0 times below the amount of the surface fungal spores in the enclosure before performing steps a) through j).

2. The method of claim 1, wherein the airborne particles are fewer than 300,000 particles per cubic meter of air.

3. The method of claim 1, wherein the amount of airborne fungal spores in the enclosure is at least 1.5 times below the amount of airborne fungal spores of the air outside the enclosure before performing steps a) through j).

4. The method of claim 1, wherein the amount of airborne fungal spores in the enclosure is at least 100 times lower than the amount of airborne fungal spores in the air outside the enclosure.

5. The method of claim 1, wherein the amount of surface fungal spores in the enclosure is at least 5 times below the amount of surface fungal spores in the enclosure before performing steps a) through j).

6. The method of claim 1, wherein the first antimicrobial agent is 2-bromo-2-nitropropane-1,3-diol.

7. The method of claim 1, wherein the cleansing agent is a composition comprising a non-ionic surfactant, benzalkonium chloride, 2-propanol, or Di-n-alkyl ($C_8$-$C_{10}$)-N,N-dimethylammonium chloride.

8. The method of claim 7, wherein the formulation comprising the non-ionic surfactant additionally comprises hydrogen peroxide.

9. The method of claim 7, wherein the non-ionic surfactant is a polyoxyethylene fatty acid ester.

10. The method of claim 1, wherein the second antimicrobial agent is a composition comprising an aqueous organosilane, a quaternary chloride or a hydantoin resin.

11. The method of claim 1, wherein the aqueous organosilane is 0.75% by weight of the formulation comprising the aqueous organosilane.

12. The method of claim 11, wherein the aqueous organosilane is octadecylaminodimethyltrimethoxysilylpropyl ammonium chloride.

13. The method of claim 1, wherein the ozone concentration in the enclosure is between 4 parts per million and 8 parts per million before terminating the release of the ozone.

14. The method of claim 1, wherein the composition comprising tea tree oil comprises 8% tea tree oil.

15. The method of claim 14, wherein the composition comprising tea tree oil further comprises 1% lemon tea tree oil.

16. The method of claim 1, wherein the air handling system is a personal temperature air conditioner.

17. The method of claim 1, wherein the air handling system comprises ductwork.

18. The method of claim 1, wherein substantially all of the exposed surfaces are fogged with the formulation comprising the second antimicrobial agent.

19. The method of claim 1, wherein the enclosure is a hotel room, a condominium or a cruise ship cabin.

* * * * *